United States Patent
Whitcher et al.

(10) Patent No.: US 10,772,675 B2
(45) Date of Patent: Sep. 15, 2020

(54) ELECTROSURGICAL FORCEPS WITH CUP FOR SUPPORTING TINES

(71) Applicant: Kirwan Surgical Products LLC, Marshfield, MA (US)

(72) Inventors: Chadwick J. Whitcher, Kingston, MA (US); Robert T. Boyd, Kingston, MA (US)

(73) Assignee: Kirwan Surgical Products LLC, Marshfield, MA (US)

( * ) Notice: Subject to any disclaimer, the term of this patent is extended or adjusted under 35 U.S.C. 154(b) by 290 days.

(21) Appl. No.: 15/447,292

(22) Filed: Mar. 2, 2017

(65) Prior Publication Data

US 2018/0250065 A1  Sep. 6, 2018

(51) Int. Cl.
*A61B 18/14* (2006.01)
*A61B 18/00* (2006.01)

(52) U.S. Cl.
CPC ...... *A61B 18/1445* (2013.01); *A61B 2018/00452* (2013.01); *A61B 2018/00607* (2013.01); *A61B 2018/1462* (2013.01)

(58) Field of Classification Search
CPC ............ A61B 18/1442; A61B 18/1445; A61B 18/1447; A61B 18/085; A61B 2018/1462; A61B 17/29; A61B 17/2901–2948; A61B 1/00137; A61B 17/30; A61B 2017/301; A61B 2017/303; A61B 2017/305; A61B 2017/306; A61B 2017/308; A61B 2018/00607; A61B 2018/00452; H01R 4/48; H01R 11/18; H01R 43/20
See application file for complete search history.

(56) References Cited

U.S. PATENT DOCUMENTS

| | | |
|---|---|---|
| 4,041,952 A | 8/1977 | Morrison, Jr. et al. |
| 4,938,761 A | 7/1990 | Ensslin |
| 5,599,350 A | 2/1997 | Schulze et al. |
| 5,925,046 A | 7/1999 | Vogel et al. |
| 6,231,574 B1 | 5/2001 | Posthuma |
| 6,235,027 B1 | 5/2001 | Herzon |
| 6,343,961 B1 | 2/2002 | Sutter |
| 7,204,836 B2 | 4/2007 | Wagner et al. |
| 7,235,073 B2 | 6/2007 | Levine et al. |
| 7,727,255 B2 | 6/2010 | Taylor et al. |
| 2004/0162557 A1* | 8/2004 | Tetzlaff ............ A61B 18/1442 606/51 |
| 2014/0324041 A1 | 10/2014 | Bowers et al. |
| 2015/0112336 A1 | 4/2015 | Scheller et al. |
| 2016/0008052 A1 | 1/2016 | Scheller |
| 2018/0132924 A1* | 5/2018 | Hermann Fakler ...... H01R 4/48 |

FOREIGN PATENT DOCUMENTS

DE  3427947 C1  1/1986

* cited by examiner

*Primary Examiner* — Eun Hwa Kim
*Assistant Examiner* — Adam Z Minchella
(74) *Attorney, Agent, or Firm* — Verrill Dana, LLP

(57) ABSTRACT

An electrosurgical forceps incorporates a support element within an interior of a cup for supporting one or both tines at their proximal ends. The support element minimizes or prevents misalignment of the tips of the forceps during use.

12 Claims, 4 Drawing Sheets

ELECTROSURGICAL FORCEPS WITH CUP FOR SUPPORTING TINES

CROSS REFERENCE TO RELATED APPLICATIONS

N/A

STATEMENT REGARDING FEDERALLY SPONSORED RESEARCH OR DEVELOPMENT

N/A

BACKGROUND

Electrosurgical forceps have a pair of resilient tines or blades that are used for grasping and coagulating tissue. The tines are typically supported at their proximal ends in a cup filled with a potting material, such as epoxy, which solidifies within the cup. The forceps may be monopolar or bipolar. In monopolar forceps, the tines are welded or otherwise joined to form an electrode in electrical communication with an electrical generator. Current flows from the active electrode through the patient's tissue to a dispersive electrode in contact with the patient's skin (which may be at some distance from the forceps) and back to the generator. In bipolar forceps, each tine of the pair comprises an electrode in communication with an electrical generator. Current flows from one tine through the tissue to the other tine.

SUMMARY OF THE INVENTION

The invention relates to electrosurgical forceps with a cup for supporting the tines. In prior art forceps, the potting material does not always completely fill the interior of the cup, leaving air pockets in various places within the cup. Such air pockets can result in a loosening of the tines within the cup, leading to a misalignment or "scissoring" of the tips at the distal end of the forceps. The present forceps include a support element within the cup that holds the proximal ends of the forceps tines, to minimize or eliminate the "scissoring" effect or misalignment of the tips.

In some embodiments, the support element includes a collar surrounding at least a portion of a proximal end of at least one tine. One or more ribs can extend from the collar to provide additional structural support.

In some embodiments, an electrosurgical forceps includes a cup comprising a circumferentially extending wall having an outer surface, an inner surface, and an open distal end. A proximal end wall extends across a proximal end of the circumferentially extending wall and has an inner surface. A pair of openings is disposed through the proximal end wall. An interior region is defined within the inner surface of the circumferentially extending wall and the inner surface of the proximal end wall. Terminal pins are disposed in the openings in the proximal end wall, with an end portion of each terminal pin extending proximally out of the cup. The forceps includes a pair of tines, each tine being generally elongated and having a tip at a distal end and a proximal end fixed with the cup. Each tine is connected for electrical communication to one of the terminal pins. A support element within the interior region of the cup is configured to support the tines within the cup. A potting material is provided within the interior region of the cup.

In some embodiments, the support element comprises a pair of collars surrounding at least a portion of the proximal ends of the tines. In some embodiments, one or more ribs can extend from the collar across the inner surface of the proximal end wall to the inner surface of the circumferentially extending wall. In some embodiments, a connecting rib can extend between the collars. In some embodiments, at least one of the tines is supported by the support element within the cup.

DESCRIPTION OF THE DRAWINGS

The invention will be more fully understood from the following detailed description taken in conjunction with the accompanying drawings in which.

DETAILED DESCRIPTION OF THE INVENTION

Figure 1:
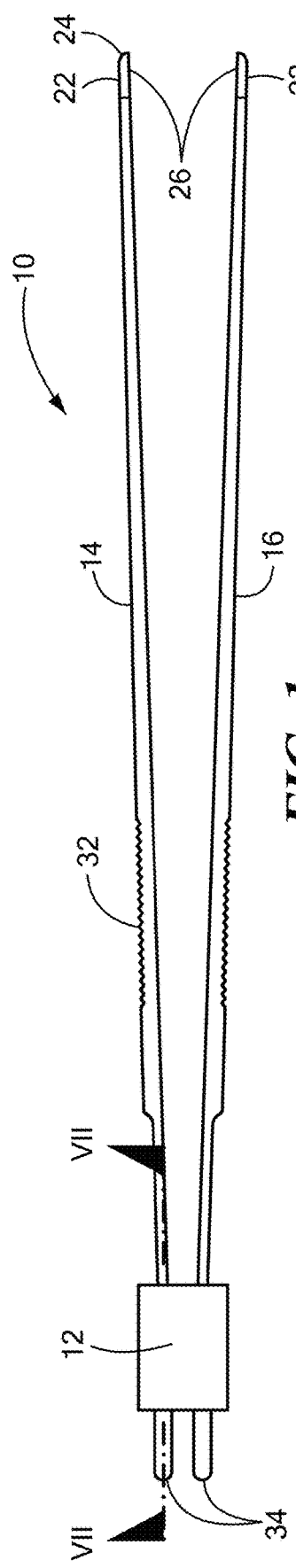
FIG. 1 is a side view of bipolar electrosurgical forceps according to an embodiment of the invention.
Figure 2:
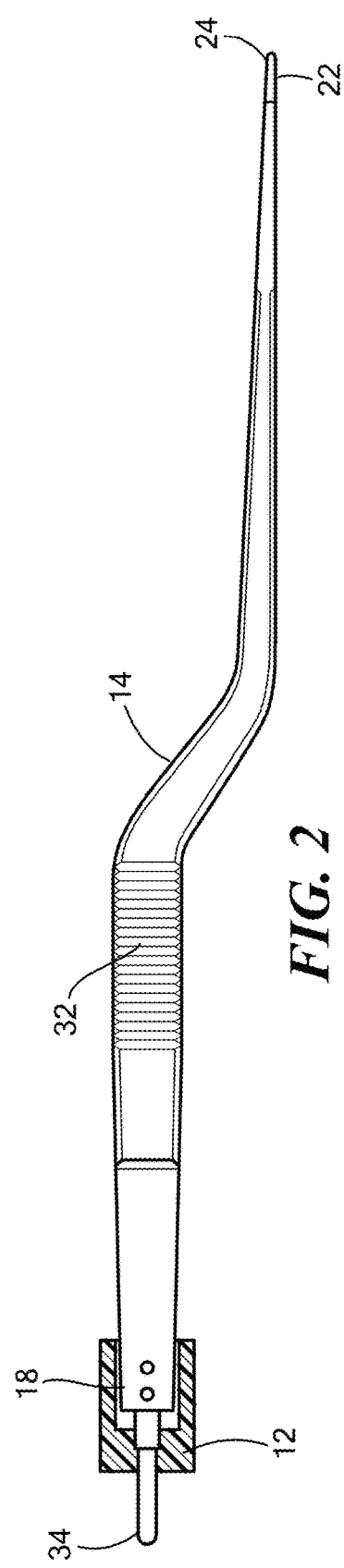
FIG. 2 is a partial cross-sectional plan view of the forceps of FIG. 1.
Figure 3:
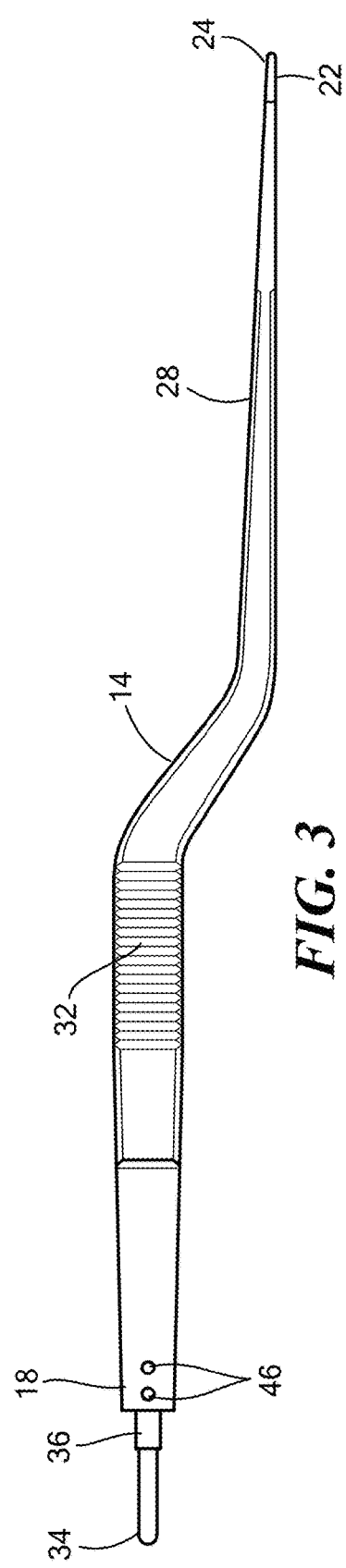
FIG. 3 is a plan view of a tine and terminal pin of the forceps of FIG. 1.

An embodiment of electrosurgical forceps 10 with a cup 12 for supporting tines 14, 16 is illustrated in FIGS. 1-3. The forceps is a bipolar device with first and second tines 14, 16 that serve as electrodes. Each of the tines is elongated and extends from a proximal end 18 supported within an electrically insulating cup 12 to a tip 22 at a distal end 24. The tines are generally flat, and the tips are configured for gripping tissue between opposed surfaces 26 when the tines are grasped by a user and squeezed closed. The tines can be electrically insulated with an insulating material 28 along most of their length from the cup 12 to a location close to the tip 22. A textured surface 32, gripping pad, or the like can be provided on each tine at a location where the tine is grasped. The proximal ends 18 are electrically connected in any suitable manner to terminal pins 34 within the cup 12. In some embodiments, the proximal end 18 of the tine includes a tab 36 to which the terminal pin is attached, such as by crimping, welding, or soldering. The proximal ends attached to the terminal pins are encapsulated within an interior region 42 of the cup 12 using a potting material 44, such as an epoxy-based material. The tines can include apertures 46 through which the potting material can flow to help affix the tines within the cup.

Figure 4:
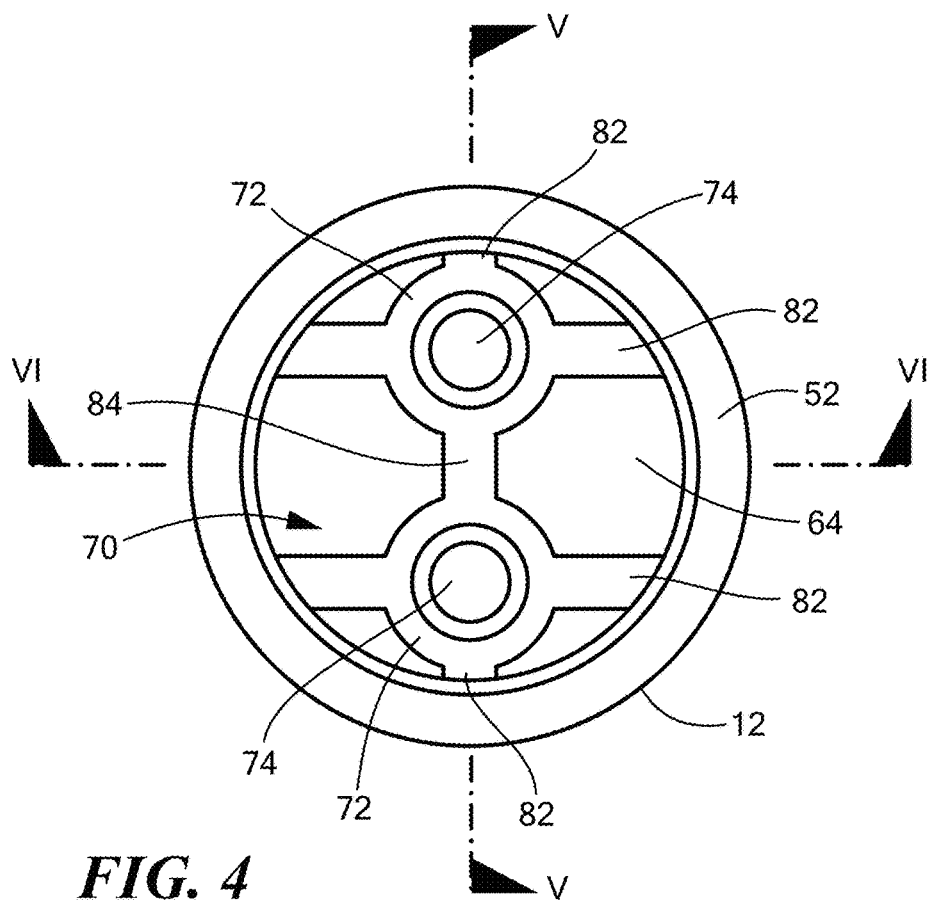
FIG. 4 is an end view of the cup of FIG. 1.
Figure 5:
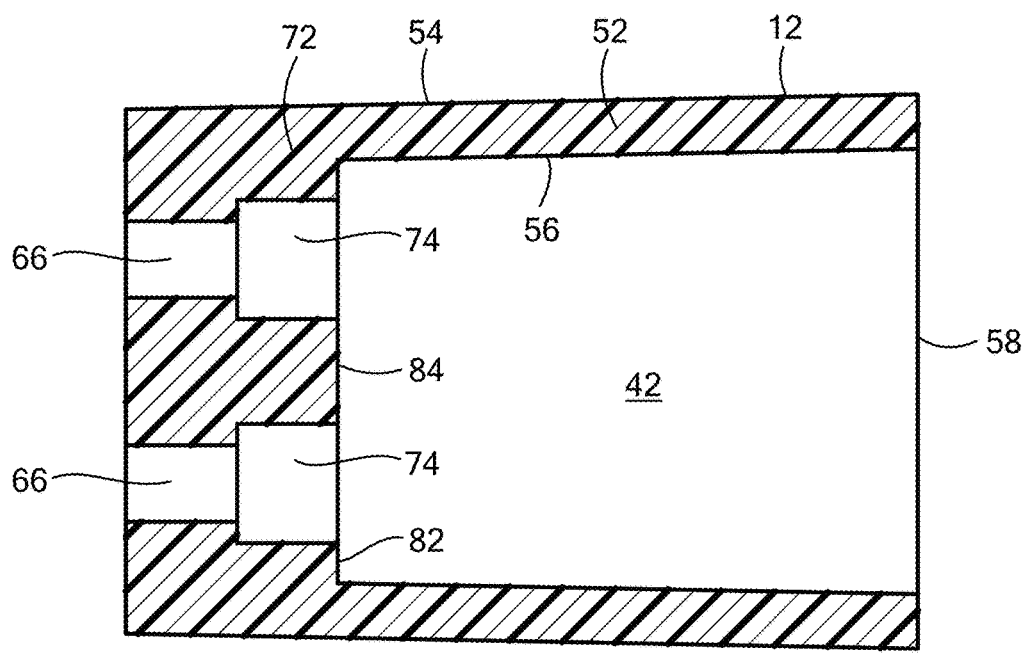
FIG. 5 a cross-sectional view along line V-V of FIG. 4.
Figure 6:
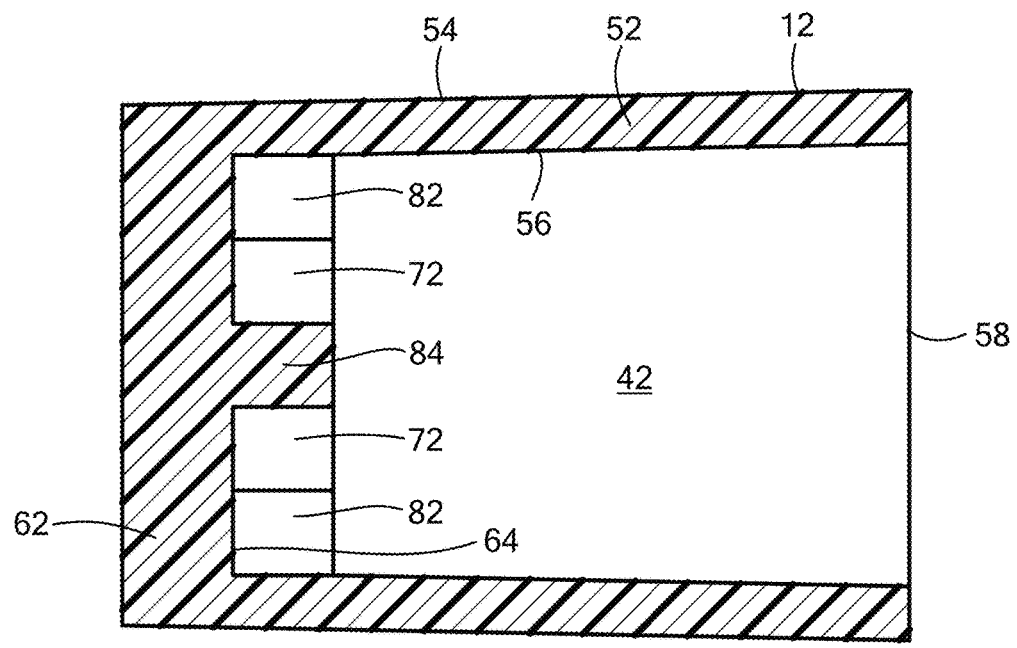
FIG. 6 is a cross-sectional view along line VI-VI of FIG. 4.
Figure 7:
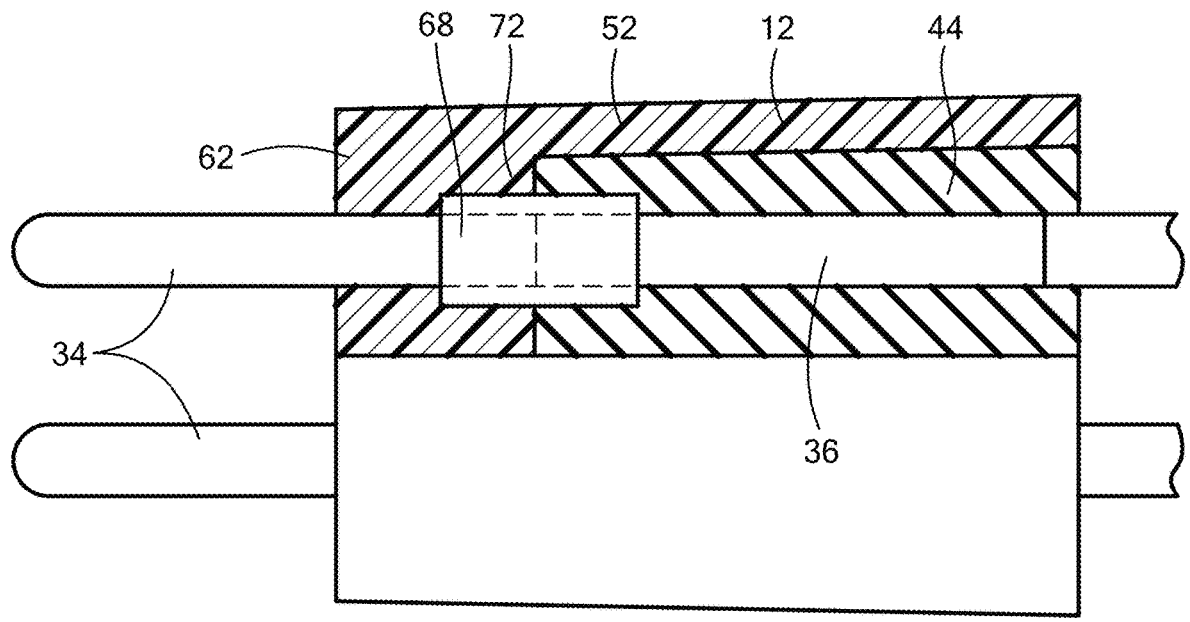
FIG. 7 is a partial cross sectional view along line VII-VII of FIG. 1.
Figure 8:
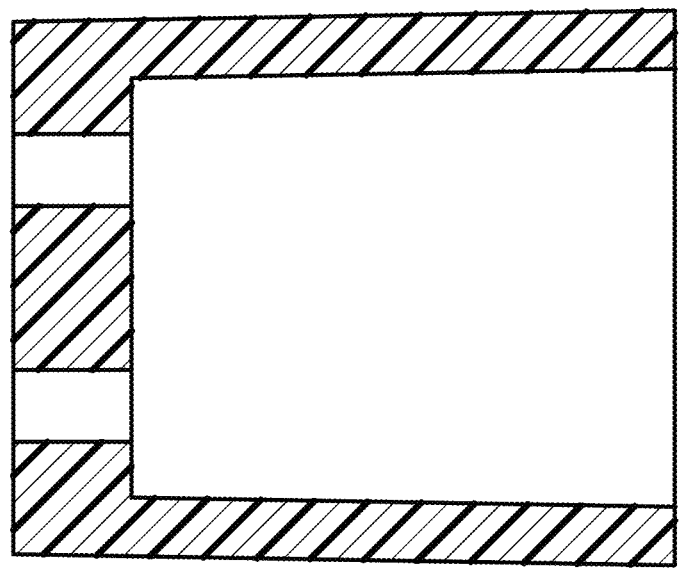
FIG. 8 is a cross-sectional view of a prior art cup.

The cup 12 includes a support element 70 (see FIG. 4, described further below) that supports one or both tines 14, 16 at their proximal ends 18 to more firmly affix the tines within the cup. More particularly, in some instances of prior art forceps, the potting material incompletely fills the cup, leaving one or more air pockets within the cup. The proximal ends of the tines are thereby prone to shifting within the cup, leading to a "scissoring" effect, by which the tips 22 of the forceps at the distal end 24 become misaligned. Such misalignment does not provide optimal operation by the forceps for grasping and coagulating tissue. (FIG. 8 illustrates a cup of a prior art forceps.) The support element 70 described herein minimizes or eliminates the risk of a "scissoring" effect or misalignment of the tips of the forceps at the distal end.

Referring more particularly to FIGS. 4-7, the cup 12 is formed with a circumferentially extending wall 52 having an outer surface 54, an inner surface 56, and an open distal end 58. A proximal end wall 62 extends across a proximal end of the circumferentially extending wall 52 and has an inner surface 64. The interior region 42 is defined within the inner surface 56 of the circumferentially extending wall 52 and the inner surface 64 of the proximal end wall 62. Two openings 66 are provided through the proximal end wall. A terminal pin 34 is disposed in each opening in the proximal end wall, with end portions of the terminal pins extending proximally out of the cup (see FIG. 7). The tab 36 of each tine is connected for electrical communication to one of the terminal pins, for example, by one or more of crimping, welding, or soldering. In the embodiment illustrated, a sleeve or crimp member 68 is illustrated.

In the embodiment shown in FIGS. 4-7, the support element includes a pair of collars 72. Each collar extends from the inner surface 64 of the proximal end wall 62 of the cup with an opening 74 in axial alignment with an associated one of the openings 66 through the proximal end wall 62. Each collar 72 surrounds at least a portion of the proximal end 18, for example, a portion of the tab 36, of one of the tines 14, 16. In some embodiments, a sleeve or crimp member 68 coaxially surrounds the tab 36 of the tine and the terminal pin 34 to maintain an electrical connection therebetween, and is disposed at least partially within the opening 74 of the collar 72. The inner diameter of the collar opening 74 can be selected so that the sleeve 68 fits firmly within the collar. In some embodiments, the collar can have an inner diameter greater than an inner diameter of the associated opening 66 in the end wall. The inner diameter of the collar can also be selected to support the tine when a sleeve or crimp member is not employed for the electrical connection between the tine and the terminal pin.

In some embodiments, the support element 70 can include one or more ribs 82 extending from one or both collars 72 across the inner surface 64 of the proximal end wall 62 to the inner surface 56 of the circumferentially extending wall 52. In some embodiments, the support element also includes a connecting rib 84 extending across the inner surface of the proximal end wall between the collars 72. The ribs add further structural rigidity to the cup. Other rib configurations can be used.

In some embodiments, the support element 70 is an annular collar that continuously surrounds the proximal end, for example, the tab, of the tine (as shown in FIGS. 4-7). In some embodiments, the collar can surround the proximal end discontinuously, as long as a sufficient amount of the proximal end is supported. For example, the collar can be provided as discontinuous circular sectors symmetrically located around the tine. In some embodiments, the opening 74 through the collar can have a circular configuration. (See FIG. 4.) In some embodiments, the opening through the collar can have a configuration complementary with the proximal end of the tine, for example, a generally rectangular configuration to mate with a generally flat tab. In some embodiments, the support element can include a single collar to support one of the tines.

The cup 12 can be made from an electrically insulating material, such as thermoplastic rubber, polypropylene, nylon, polyvinylidene fluoride (PVDF), and the like. The support element 70 can be made from the same or a different material.

The cup and support element can be manufactured in any suitable manner. In some embodiments, the cup can be manufactured by machining, injection molding, overmolding, casting, or by one of several additive manufacturing methods, such as stereolithography, fused deposition, or selective sintering. In some embodiments, the support element can be manufactured integrally with the cup. In some embodiments, the support element can be manufactured separately from the cup and affixed within the interior region of the cup in any suitable manner, such as by adhesive, sonic welding, or the like.

The tines 14, 16 can be made from a material, such as stainless steel, nickel, aluminum, or titanium, or alloys thereof, that provides suitable strength and electrical conductivity. The tip can be made of the same or a different electrically conductive material. The tip can be integral with a body of the tine, or the tip can be attached to the body of the tine in any suitable manner, such as brazing, to facilitate electrical conductivity between the body and the tip and to withstand breakage under typical usage.

The forceps can be fabricated in any suitable manner. In one embodiment, an electrically conductive material for the tines is extruded or otherwise provided in sheet form. The sheet can be drawn or rolled to achieve a desired final thickness dimension for the tine bodies. The tines are stamped from the sheet in the desired configuration. If the tips are formed separately from the bodies, the tips are attached to the body, for example, by brazing. Serrations for finger grips, if present, can be stamped into a midportion of the tines to aid a physician in gripping the forceps during use.

A rear or spring section can be cold formed, as by rolling, to compress its thickness and to work harden the material. Work hardening of the material in this section strengthens the material, enabling a physician to squeeze the tines together repeatedly to grasp tissue and release the tines to return to their rest position.

The perimeter of the strip is stamped to form the general shape of the tine. The tine can have a generally straight configuration, or the tine can have bends along its length (as shown in FIGS. 2-3), depending on the particular application. The perimeter of the tine is formed, as by a coining process, to form the edges. The tab is stamped, deburred, and formed at the proximal end of the tine. The terminal pins can be attached to the tabs in any suitable manner, such as by crimping, welding, or soldering. Apertures can be stamped into the proximal end to allow the potting material to flow through and around the tine. Openings for gripping pads, if present, can be stamped or cut in the tines.

The tines with attached terminal pins are inserted through the openings in the cup. The potting material is placed within the cup and cured.

Additional aspects include the following:

1. An electrosurgical forceps comprising:
    a cup comprising:
        a circumferentially extending wall having an outer surface, an inner surface, and an open distal end,
        a proximal end wall extending across a proximal end of the circumferentially extending wall and having an inner surface, at least one opening disposed through the proximal end wall, and
        an interior region defined within the inner surface of the circumferentially extending wall and the inner surface of the proximal end wall;
    a terminal pin disposed in the at least one opening in the proximal end wall, an end portion of the terminal pin extending proximally out of the cup;
    a pair of tines, each tine being generally elongated and having a tip at a distal end and a proximal end fixed with the cup, one tine of the pair of tines connected for electrical communication to the terminal pin;
a support element within the interior region of the cup configured to support at least the one tine of the pair of tines within the cup; and
a potting material within the interior region of the cup.
2. The forceps of embodiment 1, wherein the support element comprises a collar surrounding at least a portion of the proximal end of the one tine.
3. The forceps of embodiment 2, wherein the collar is coaxial with the at least one opening.
4. The forceps of any of embodiments 2-3, wherein the collar has an inner diameter greater than an inner diameter of the at least one opening.
5. The forceps of any of embodiments 2-4, wherein the support element further comprises one or more ribs extending from the collar across the inner surface of the proximal end wall to the inner surface of the circumferentially extending wall.
6. The forceps of any of embodiments 2-5, wherein the support element comprises a second collar surrounding at least a portion of the proximal end of the second tine.
7. The forceps of embodiment 6, wherein the support element further comprises one or more additional ribs extending from the second collar across the inner surface of the proximal end wall to the inner surface of the circumferentially extending wall.
8. The forceps of any of embodiments 6-7, wherein the support element further comprises a connecting rib extending across the inner surface of the proximal end wall between the collar and the second collar.
9. The forceps of any of embodiments 1-8, further comprising a sleeve or crimp member coaxially surrounding the one tine and the terminal pin at least partially within the support element.
10. The forceps of an of embodiments 1-9, further comprising a second opening disposed through the proximal end wall of the cup, a second terminal pin disposed in the second opening in the proximal end wall, an end portion of the second terminal pin extending proximally out of the cup, and a second tine of the pair of tines connected for electrical communication to the second terminal pin; and
wherein the support element is configured to support the second tine within the cup.
11. The forceps of any of embodiments 1-10, wherein the potting material comprises an epoxy.
12. The forceps of any of embodiments 1-11, wherein the circumferentially extending wall is generally cylindrical.
13. A method of forming the electrosurgical forceps of any of embodiments 1-12, comprising:
providing the pair of tines and the terminal pin;
attaching the one tine of the pair of tines to the terminal pin for electrical communication;
mounting the pair of tines and the one terminal pin to the cup with the support element supporting the one tine or both tines of the pair of tines; and
filling the cup with a potting material.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:
1. An electrosurgical forceps comprising:
an electrically insulating cup comprising:
a circumferentially extending wall having an outer surface, an inner surface, and an open distal end,
a proximal end wall extending across a proximal end of the circumferentially extending wall and having an inner surface, at least one opening disposed through the proximal end wall, and
an interior region defined within the inner surface of the circumferentially extending wall and the inner surface of the proximal end wall;
a terminal pin disposed in the at least one opening in the proximal end wall, an end portion of the terminal pin extending proximally out of the cup;
a pair of tines, each tine being generally elongated and having a tip at a distal end and a proximal end fixed within the cup, one tine of the pair of tines is connected for electrical communication to the terminal pin;
wherein the cup includes an electrically insulating support element comprising a collar within the interior region of the cup configured to support at least the one tine of the pair of tines within the cup, wherein the collar surrounds at least a portion of the proximal end of the one tine and/or the terminal pin, the collar extending from the inner surface of the proximal end wall and spaced from the inner surface of the circumferentially extending wall; and
a potting material within the interior region of the cup.
2. The forceps of claim 1, wherein the collar is coaxial with the at least one opening.
3. The forceps of claim 1, wherein the collar has an inner diameter greater than an inner diameter of the at least one opening.
4. The forceps of claim 1, wherein the support element further comprises one or more ribs extending from the collar across the inner surface of the proximal end wall to the inner surface of the circumferentially extending wall.
5. The forceps of claim 1, wherein the support element comprises a second collar surrounding at least a portion of the proximal end of a second tine of the pair of tines and/or a second terminal pin.
6. The forceps of claim 5, wherein the support element further comprises one or more additional ribs extending from the second collar across the inner surface of the proximal end wall to the inner surface of the circumferentially extending wall.

7. The forceps of claim 5, wherein the support element further comprises a connecting rib extending across the inner surface of the proximal end wall between the collar and the second collar.

8. The forceps of claim 1, further comprising a sleeve or crimp member coaxially surrounding the one tine and the terminal pin at least partially within the support element.

9. The forceps of claim 1, further comprising a second opening disposed through the proximal end wall of the cup, a second terminal pin disposed in the second opening in the proximal end wall, an end portion of the second terminal pin extending proximally out of the cup, and a second tine of the pair of tines connected for electrical communication to the second terminal pin; and
    wherein the support element is configured to support the second tine within the cup.

10. The forceps of claim 1, wherein the potting material comprises an epoxy.

11. The forceps of claim 1, wherein the circumferentially extending wall is generally cylindrical.

12. A method of forming an electrosurgical forceps, comprising:
    providing a pair of tines and a terminal pin, each tine being generally elongated and having a proximal end and a tip at a distal end, one tine of the pair of tines connectable for electrical communication to the terminal pin;
    providing an electrically insulating cup comprising: a circumferentially extending wall having an outer surface, an inner surface, and an open distal end,
    a proximal end wall extending across a proximal end of the circumferentially extending wall and having an inner surface, the at least one opening disposed through the proximal end wall,
    an interior region defined within the inner surface of the circumferentially extending wall and the inner surface of the proximal end wall, and
    an electrically insulating support element comprising a collar within the interior region of the cup, the collar configured to surround at least a portion of the proximal end of the one tine and/or the terminal pin, the collar extending from the inner surface of the proximal end wall and spaced from the inner surface of the circumferentially extending wall;
    attaching the one tine of the pair of tines to the terminal pin for electrical communication; mounting the pair of tines and the one terminal pin to the cup with the support element supporting the one tine or both tines of the pair of tines; and
    filling the cup with a potting material.

\* \* \* \* \*